United States Patent [19]

Silverstein et al.

[11] Patent Number: 4,462,408
[45] Date of Patent: Jul. 31, 1984

[54] ULTRASONIC ENDOSCOPE HAVING ELONGATED ARRAY MOUNTED IN MANNER ALLOWING IT TO REMAIN FLEXIBLE

[75] Inventors: Fred E. Silverstein, Seattle; David Giuliani, Mercer Island, both of Wash.

[73] Assignee: Advanced Technology Laboratories, Inc., Bellevue, Wash.

[21] Appl. No.: 379,213

[22] Filed: May 17, 1982

[51] Int. Cl.³ .............................................. A61B 10/00
[52] U.S. Cl. ........................................ 128/660; 128/4
[58] Field of Search ................. 128/4, 24 A, 660–663

[56] References Cited

U.S. PATENT DOCUMENTS

| | | | |
|---|---|---|---|
| 3,938,502 | 2/1976 | Bom | 128/660 |
| 4,273,111 | 6/1981 | Tsukaya | 128/660 X |
| 4,327,738 | 5/1982 | Green et al. | 128/660 |
| 4,354,501 | 10/1982 | Colley et al. | 128/660 X |

FOREIGN PATENT DOCUMENTS 168309  5/1954  Japan ........................ 128/4

Primary Examiner—William E. Kamm
Assistant Examiner—Francis J. Jaworski
Attorney, Agent, or Firm—Lawrence S. Levinson; Sanford J. Asman

[57] ABSTRACT

The invention is a fiber-optic endoscope which has an elongated ultrasonic array, such as a linear array or a phased array. The array is mounted on either the distal portion of the bending section (not under operator control) portion of the endoscopic tube or on the proximal portion of bendable portion of the tube. Thus, the present invention includes both a fiber-optic endoscope and an ultrasonic transducer. Yet, the presence of the ultrasonic transducer does not interfere with the operation of the placement of the fiber-optic probe.

10 Claims, 2 Drawing Figures

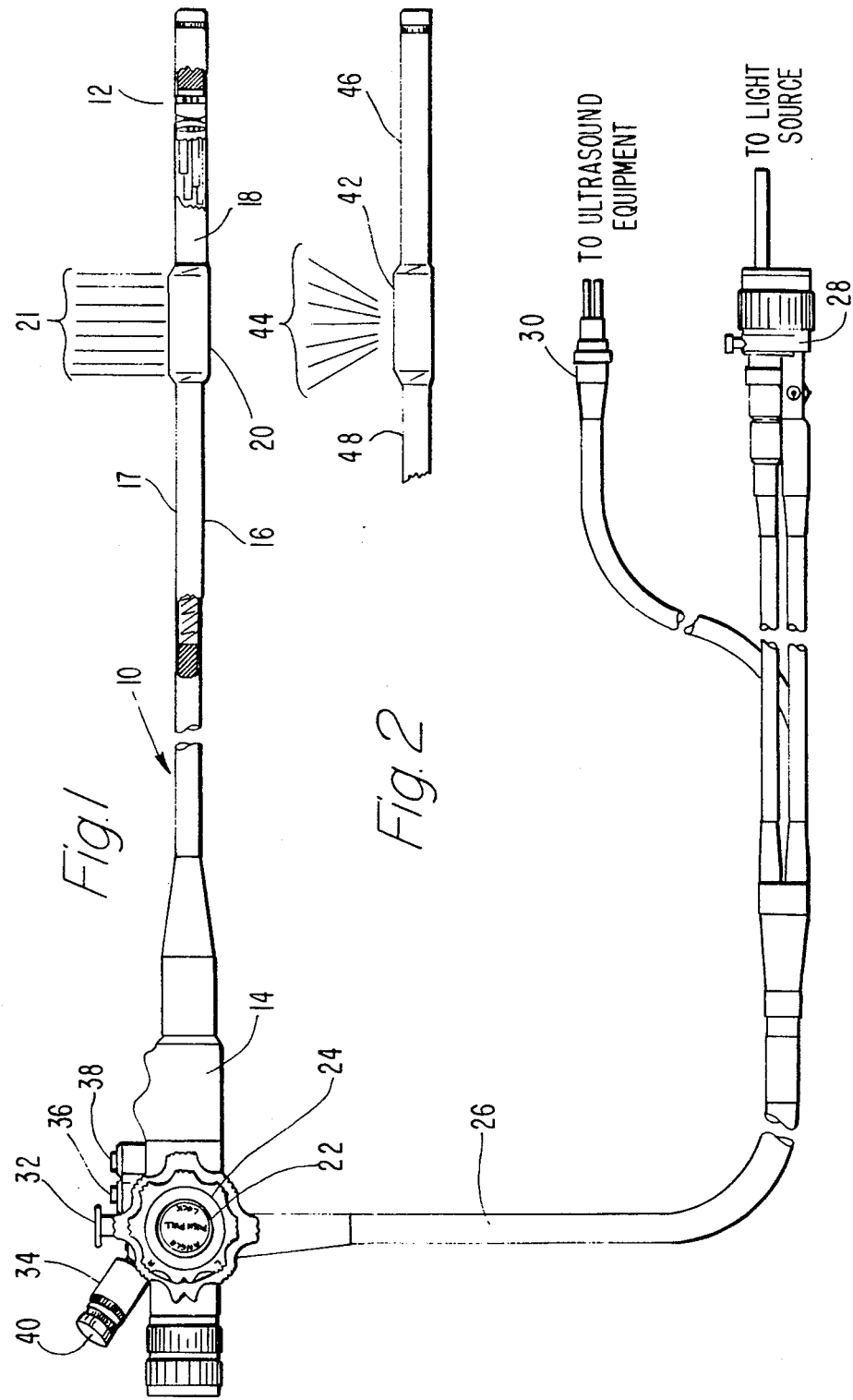

ULTRASONIC ENDOSCOPE HAVING ELONGATED ARRAY MOUNTED IN MANNER ALLOWING IT TO REMAIN FLEXIBLE

BACKGROUND OF THE INVENTION

The present invention relates to endoscopes of the type which include an elongated ultrasonic transducer, such as a linear transducer or a phased array transducer.

Endoscopes are devices which are used for the visual inspection of internal organs of living bodies. They typically include a tube, which may be flexible or rigid, which extends between a control housing at its proximal end and a tip or probe at its distal end. A bendable tube portion is included adjacent to the probe. The bendable portion is bent under operator control through the use of a control mechanism mounted on the control housing. Optical illuminating and viewing means, which include an objective lens in the probe and an eyepiece in the control housing, are provided. The optical means are used to view the interior surfaces of the body cavities through which the endoscope passes.

While an endoscope provides an operator with information concerning interior surface conditions, the need for ultrasonic imaging of underlying surfaces and interior organs has been recognized, and heretofore, endoscopic probes containing ultrasonic tranducers were known. One such probe was described in U.S. Pat. No. 3,938,502 entitled APPARATUS WITH A CATHETER FOR EXAMINING HOLLOW ORGANS OR BODIES WITH THE ULTRASONIC WAVES which issued on Feb. 17, 1976. That probe, however, lacked optical viewing means. Optical viewing means are needed to permit an operator to position the ultrasonic probe at a desired location within a patient's body. Without knowledge of transducer location and orientation, any ultrasonic image obtained is of minimal diagnostic use. Additionally, optical viewing means are generally required to safely guide a probe as it is inserted into a patient's body, in order to avoid harming the patient.

Endoscopes have heretofore been provided with linear ultrasonic transducer arrays at their distal ends. For example, U.S. Pat. No. 4,273,111 entitled ENDOSCOPE WITH BEND ANGLE CONTROL which issued to T. Tsukaya on June 16, 1981 describes an endoscope with a freely bendable section which includes a number of "supersonic transducers" at its distal end. While such endoscopes are able to provide simultaneous visual and ultrasonic imaging of internal body parts, a problem which has been encountered when such an endoscope is inserted into a body cavity is that the elongated, inflexible section housing the transducer interferes with the operator's ability to move the bendable, distal portion of the endoscope.

One endoscope, which appears in Japanese Pat. No. 55-168309, has a series of circumferentially placed transducers which are set back somewhat from the extreme distal end of the endoscope. The invention described in that patent is primarily concerned with providing an endoscope for producing tomographic images, i.e., images which correspond to slices taken in a plane perpendicular to the longitudinal axis of the body. In particular, the invention described in that patent is an endoscope which has an outlet port through which water can be pumped into the stomach. The purpose of pumping water into the stomach, as described therein, is to displace any gas present in the stomach whereby a better interface match for the ultrasound is provided. That endoscope also includes a relatively wide diameter tip at the distal end of the probe. The wide tip is intended to block the duodenum to prevent water, which is pumped into the stomach, from flowing out into the duodenum.

SUMMARY OF THE INVENTION

The present invention is intended to provide an improved fiber-optic endoscope which is insertable into a body cavity, and which includes an elongated rectilinear or phased array ultrasonic transducer for imaging internal body parts. It is intended that the ultrasonic array be placed at the end of the "insertion tube" portion of the endoscope in order that it not interfere with the operator's positioning of the "bending section" of the endoscope.

In order to accomplish this goal, the present invention comprises an endoscope having a probe connected by an insertion tube to a control housing. The instrument includes an optical illuminating and viewing system, which typically includes an objective lens located in the distal end of the probe and an eyepiece in the housing. The eyepiece is used for optically viewing internal surfaces of body parts through which the endoscope passes. At least a portion of the tube adjacent to the probe is bendable under operator control. Controls in a handle at the control housing provide means, which allow an operator to control the bending section of the endoscope. The bending section can be directed by the operator in a desired direction to facilitate guiding the probe into a particular body part, so the probe can be located in a desired location therewithin. Ultrasonic imaging of underlying tissue at optically-identified areas is provided by means of a pulsed ultrasonic imaging system. An elongated transducer array is preferably located either on the proximal portion of the distal end of the bending section of the tube or on the distal portion of the insertion tube. Coaxial cables connect individual transducer elements of the array to a pulse generator and to pulse receiver means in the standard manner. Means are provided for transmitting and receiving ultrasonic energy.

With the present invention, high resolution ultrasonic images are obtained over a range of depths beneath the surface of the body part. A removable eyepiece at the housing is used for direct viewing by the operator while the endoscope probe is guided into the desired position in the body cavity. Means are also provided for viewing the optical image by a video camera having an output connected to a monitor which is typically placed adjacent to the ultrasonic image display. Consequently, both the optical and ultrasonic images are simultaneously displayable and viewable by the operator.

BRIEF DESCRIPTION OF THE DRAWING

In the Drawing:

FIG. 1 is a perspective view of an endoscope and which includes the ultrasonic imaging system of the present invention; and FIG. 2 is a partial perspective view of an alternative embodiment of the present invention on an endoscope which includes two bendable portions with the ultrasonic imaging system of the present invention located therebetween.

DETAILED DESCRIPTION OF THE PREFERRED EMBODIMENT

Referring generally to FIG. 1, the endoscope 10 of the present invention is shown. The endoscope 10 comprises a fiber-optic probe 12 connected to a housing 14 by an elongated tube 16. A portion 18 of the tube 16 adjacent to the probe 12 is bendable. The term "bendable" is used herein to indicate that the portion 18 can be bent under the control of an operator, as will be more fully explained hereinafter. Thus, the non-bendable insertion portion 17 of the tube 16 is generally flexible, but it is not bendable under the control of an operator. An ultrasonic trandsucer 20, such as the linear ultrasonic array having an ultrasonic field of view 21, is mounted at the proximal end of the fiber-optic probe 12. Alternatively, the array 20 could be mounted at the distal end of the non-bendable portion 17 of the tube 16.

The present endoscope 10 further comprises a control unit 22 which is located in the housing 14 at the proximal end of the tube 16. The control unit 22 includes means 24 for controlling the bending section 18 of the probe 12. Such means 24 typically allow the operator to control the "up-down" and "left-right" movement of the bending section 18 of the probe 12. A set 26 of conventional, flexible bundles which include conductors of light and ultrasound energy 28, 30, extend away from the control unit 22, to connect to appropriate light producing and image displaying apparatus and to ultrasound producing and displaying apparatus (not shown) in a manner generally used, and well known, in the art.

The endoscope 10 of the present invention is substantially conventional in design. However, it is distinguished from prior endoscopes in that it includes a linear ultrasonic transducer 20 which is displaced away from the distal end of the bending section 18 of the tube 16, rather than at distal end of the probe 12. As will be understood by those skilled in the art, the portion of the transducer 20 is selected, in accordance with the present invention, to be in a location where it will not interfere with the control of the probe 12 by the operator.

While the preferred embodiment of the invention makes use of a linear array transducer 20, those of ordinary skill in the art will recognize that a phased array transducer could be substituted for the present linear array transducer without departing from the spirit or scope of the present invention. Accordingly, in an alternative embodiment of the invention, shown in FIG. 2, a phased array transducer 42, having an ultrasonic field of view 44, is located between a pair of bendable tubes 46, 48. It is therefore, comtemplated that the present invention can be used either with a linear array or a phased array, and that in either event, it is displaced away from the distal end of the probe.

An important feature which distinguishes the present invention from the earlier noted Japanese invention, is that in the elongated transducer is not mounted between the bending section 18 and the distal end of the probe 12, but rather between the insertion tube portion of the tube 16 and the bending section 18. Another distinguishing feature of the present invention is that the transducer array 20 is either a linear array or a phased array, i.e. it is an array which is elongated (in the direction of the axis of the tube 16). Thus, rather than providing a tomographic ultrasonic scan of a slice through a patient, the present invention may be employed to provide an elongated image of a particular, selected organ.

A particular advantage of the present invention over the fiber-optic endoscopes of the prior art is that after the endoscope of the present invention is positioned in the stomach of a patient, the operator can bend the distal end of the probe 12 back on itself in order to visually observe the specific orientation of the array 20. Thus, the operator has actual, visual confirmation of the position of the array and he therefore knows the specific orientation of the array 20, so that he can properly correlate the ultrasonic image of with the visual positioning of the probe.

While the inventive features of the present invention have been described, other standard features of fiber-optic endoscopes which include a water valve 32, a forceps inlet 34, and air switch 36, a suction switch 38, and an eyepiece section 40, all of which are located on the housing 14, are considered well known. Accordingly, they will not be more fully described herein. Similarly, the means for connecting the optical fibers and electronic controls, and the particular electronics and optics used to produce and interpret ultrasound and light transmissions and reception in the present invention, are considered to be obvious to those of ordinary skill in the art, and they are not fully described herein, although their use is contemplated with the present invention.

We claim:

1. An improved fiber-optic endoscope of the type comprising:
   (a) a tube having a bending section which can be bent under operator control, which tube includes a distal end portion which contains light transmitting and receiving means;
   (b) a control unit with which an operator can control, through control means, the position of said distal portion;
   (c) an intermediate insertion portion of said tube between said distal portion and said control unit; and
   (d) an elongated ultrasonic transducer of the type which provides cross-sectional images through a portion of the body, which transducer is mounted on said tube,
   wherein the improvement comprises the elongated ultrasonic transducer being mounted on the distal end of said insertion portion of said tube.

2. The improved fiber-optic endoscope of claim 1 wherein said elongated untrasonic transducer has its long axis mounted along the axis of said tube.

3. The improved fiber-optic endoscope of claim 2 wherein said elongated ultrasonic transducer is comprised of a linear array of multiple transducers, and said multiple transducers are aligned along the axis of said tube.

4. The improved fiber-optic endoscope of claim 2 wherein said elongated ultrasonic transducer is comprised of a phased array of multiple transducers, and said multiple transducers are aligned along the axis of said tube.

5. The improved fiber-optic endoscope of claim 1 wherein said insertion portion of said tube includes at least a second bending section and said elongated ultrasonic transducer is mounted between said bending section of said tube.

6. An improved fiber-optic endoscope of the type comprising: (a) a tube having a bending section which can be bent under operator control, which tube includes a distal end portion which contains a light transmitting and receiving means;

(b) a control unit with which an operator can control, through control means, the position of said distal portion;
(c) an intermediate insertion portion of said tube between said distal portion and said control unit; and
(d) an elongated ultrasonic transducer of the type which provides cross-sectional images through a portion of the the body, which transducer is mounted on said tube, wherein the improvement comprises the elongated ultrasonic transducer being mounted on the proximal end of said bending section of said tube that said light transmitting and receiving means can be bent back, under operator control, to observe said transducer.

7. The improved fiber-optic endoscope of claim 6 wherein said elongated ultrasonic transducer has its long axis mounted along the axis of said tube.

8. The improved fiber-optic endoscope of claim 7 wherein said elongated ultrasonic transducer is comprised of a linear array of multiple transducers, and said multiple transducers are aligned along the axis of said tube.

9. The improved fiber-optic endoscope of claim 7 wherein said elongated ultrasonic transducer is comprised of a phased array of multiple transducers, and said multiple transducers are aligned along the axis of said tube.

10. The improved fiber-optic endoscope of claim 6 wherein said insertion portion of said tube includes at least a second bending section and said elongated ultrasonic transducer is mounted between said bending sections of said tube.

* * * * *

UNITED STATES PATENT AND TRADEMARK OFFICE
CERTIFICATE OF CORRECTION

PATENT NO. : 4,462,408

DATED : July 31, 1984

INVENTOR(S) : Fred E. Silverstein, David Giuliani

It is certified that error appears in the above-identified patent and that said Letters Patent is hereby corrected as shown below:

Claim 5, Column 4, line 63:
"tion" should read --tions--

Claim 6, Column 5, line 15;
after "tube" insert --such--

Signed and Sealed this

Twenty-sixth Day of February 1985

[SEAL]

*Attest:*

DONALD J. QUIGG

*Attesting Officer*  Acting Commissioner of Patents and Trademarks